(12) United States Patent
Nakajima et al.

(10) Patent No.: US 11,020,009 B2
(45) Date of Patent: Jun. 1, 2021

(54) USER TERMINAL

(71) Applicants: OMRON CORPORATION, Kyoto (JP); OMRON HEALTHCARE CO., LTD., Kyoto (JP)

(72) Inventors: Hiroshi Nakajima, Kyoto (JP); Hirotaka Wada, Kyoto (JP); Tamio Ueda, Takatsuki (JP); Daisuke Nozaki, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 30 days.

(21) Appl. No.: 16/460,257

(22) Filed: Jul. 2, 2019

(65) Prior Publication Data

US 2019/0320910 A1    Oct. 24, 2019

Related U.S. Application Data

(63) Continuation of application No. PCT/JP2017/044394, filed on Dec. 11, 2017.

(30) Foreign Application Priority Data

Jan. 4, 2017 (JP) ............................. JP2017-000247

(51) Int. Cl.
*A61B 5/021* (2006.01)
*A61B 5/01* (2006.01)
(Continued)

(52) U.S. Cl.
CPC ............... *A61B 5/021* (2013.01); *A61B 5/01* (2013.01); *A61B 5/4809* (2013.01); *A61B 5/681* (2013.01);
(Continued)

(58) Field of Classification Search
CPC .... A61B 2562/0219; A61B 2562/0247; A61B 2562/0271; A61B 5/00; A61B 5/01;
(Continued)

(56) References Cited

U.S. PATENT DOCUMENTS 8,251,913 B2 * 8/2012 Takahashi .............. A61B 5/022
600/485
2002/0156352 A1  10/2002 Eggers
(Continued)

FOREIGN PATENT DOCUMENTS

JP   2004-529704   9/2004
JP   2013-208283   10/2013
(Continued)

OTHER PUBLICATIONS

International Preliminary Report on Patentability dated Jul. 4, 2019 in International (PCT) Application No. PCT/JP2017/044394.
(Continued)

*Primary Examiner* — Niketa I Patel
*Assistant Examiner* — Vynn V Huh
(74) *Attorney, Agent, or Firm* — Wenderoth, Lind & Ponack, L.L.P.

(57) ABSTRACT

According to an embodiment, a user terminal includes a processor; a blood pressure sensor; and a temperature sensor. The processor is configured to control whether or not to enable transmission of the blood pressure data obtained by the blood pressure sensor based on whether or not any of at least one transmission condition is satisfied; and transmit the blood pressure data when the transmission of the blood pressure data was enabled. The transmission condition include a condition satisfied when a fluctuation of temperature in a latest unit time of measurement time of the blood
(Continued)

pressure data exceeds a threshold, the temperature being indicated by the temperature data obtained by the temperature sensor.

4 Claims, 3 Drawing Sheets

(51) Int. Cl.
*A61B 5/00* (2006.01)
*G16H 40/67* (2018.01)
*G16H 40/63* (2018.01)
*G06Q 50/22* (2018.01)

(52) U.S. Cl.
CPC ............. *A61B 2562/0219* (2013.01); *A61B 2562/0247* (2013.01); *A61B 2562/0271* (2013.01)

(58) Field of Classification Search
CPC ....... A61B 5/021; A61B 5/022; A61B 5/4809; A61B 5/681; G06Q 50/22
See application file for complete search history.

(56) References Cited

U.S. PATENT DOCUMENTS

| | | |
|---|---|---|
| 2013/0261404 A1 | 10/2013 | Sato et al. |
| 2015/0119726 A1 | 4/2015 | Matsuno et al. |
| 2017/0224244 A1 | 8/2017 | Kuwabara et al. |
| 2018/0042486 A1 | 2/2018 | Yoshizawa et al. |
| 2019/0380662 A1* | 12/2019 | Kwan .................... A61B 5/117 |

FOREIGN PATENT DOCUMENTS

| | | |
|---|---|---|
| JP | 2015-084797 | 5/2015 |
| JP | 2015-154988 | 8/2015 |
| JP | 2016-087002 | 5/2016 |
| JP | 2016-190022 | 11/2016 |
| WO | 2016/024495 | 2/2016 |

OTHER PUBLICATIONS

International Search Report dated Feb. 20, 2018 in International (PCT) Application No. PCT/JP2017/044394 with English translation.

Decision to Grant a Patent dated Oct. 27, 2020 in corresponding Japanese Patent Application No. 2017-000247, with Machine English translation.

* cited by examiner

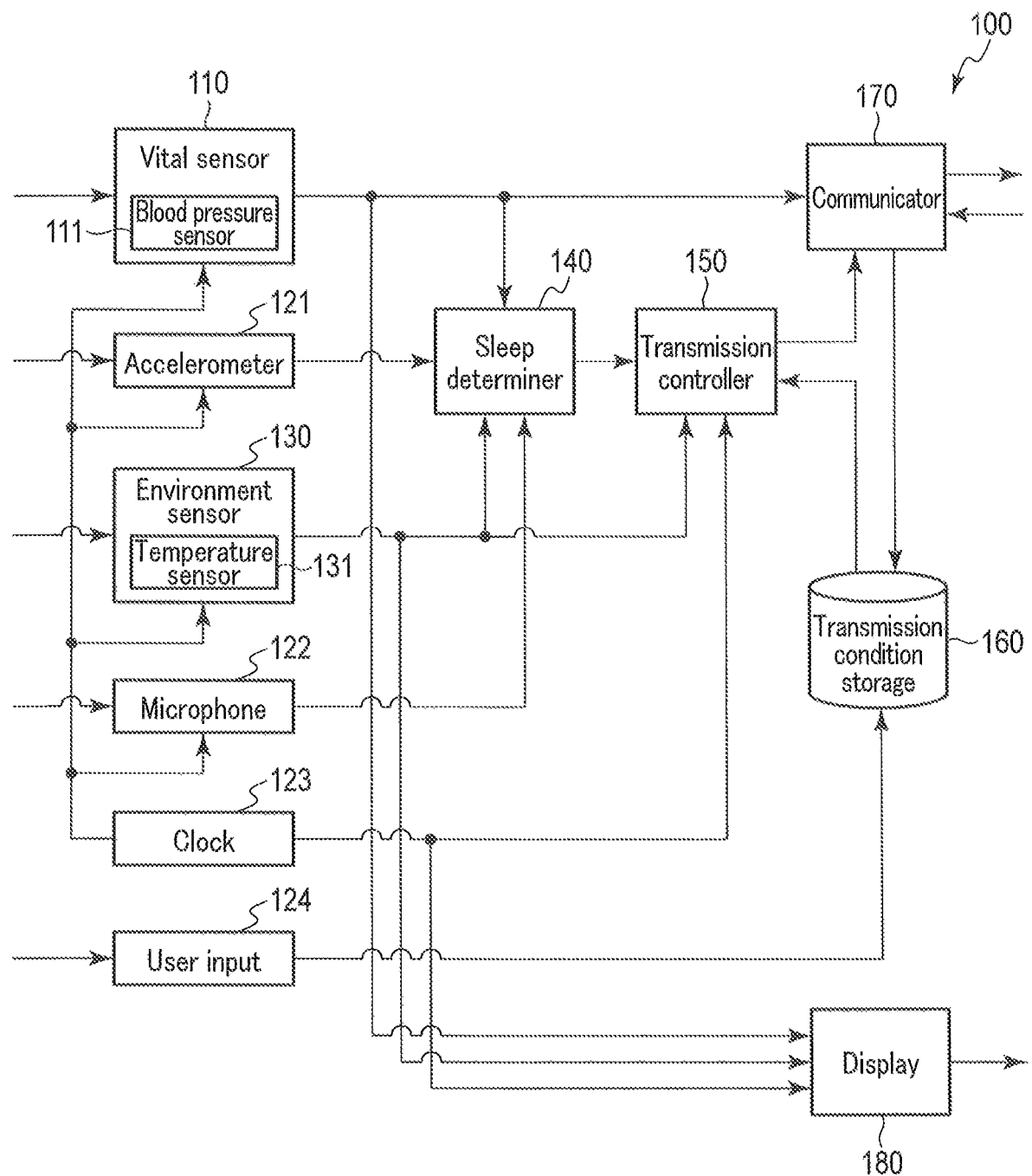
F I G. 1

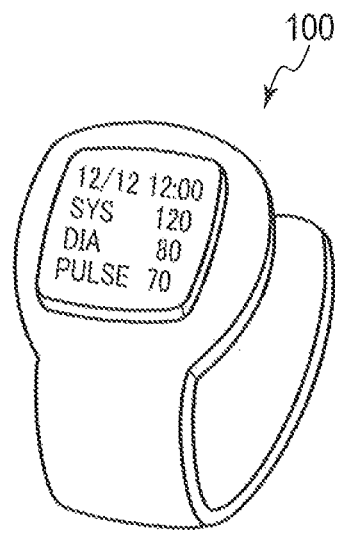
F I G. 2
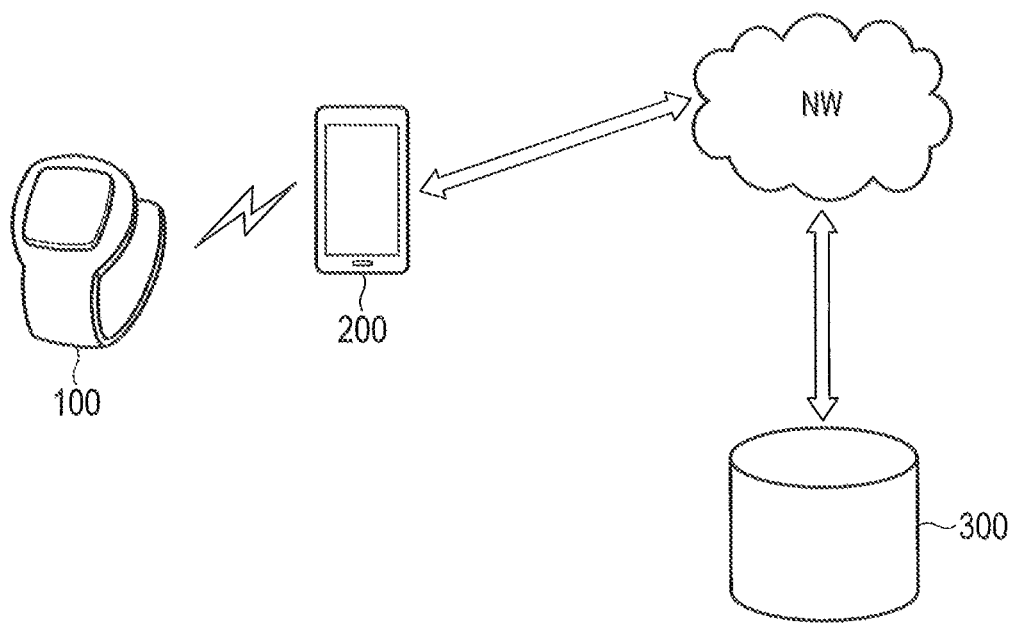
F I G. 3

USER TERMINAL

CROSS-REFERENCE TO RELATED APPLICATIONS

This application is a Continuation Application of PCT Application No. PCT/JP2017/044394, filed Dec. 11, 2017, the entire contents of which are incorporated herein by reference.

FIELD

Embodiments described herein relate to a data transmission technique in a user terminal that measures vital information.

BACKGROUND

It is desirable for patients with abnormal blood pressure (typically high blood pressure) to have their blood pressure managed on a daily basis. Unfortunately, conventional stationary blood pressure measurement devices are difficult to carry around. Thus, a user is plagued by a heavy burden when measuring blood pressure at his or her workplace or any other locations outside the home. On top of that, it is extremely difficult to capture sharp blood pressure fluctuation that could lead to a risk of developing a cerebrovascular or cardiovascular disease, with blood pressure measurement performed only several times a day.

In recent years, the development of sensor technology has yielded user terminals that are simply worn on a wrist of a user for example to enable the user to measure his or her blood pressure. Such a user terminal enables the user to timely measure his or her blood pressure while being free of the heavy burden. Such user terminals employ schemes such as tonometry for example to be capable of implementing continuous measurement of a user' blood pressure on a beat-to-beat basis.

Continuous measurement of user's vital information means that a large amount of the user's vital data is generated. For example, since human's daily heart rate is about 100,000, blood pressure data of about 100,000 sets per day will be generated for each user.

In order to entirely store a large amount of vital data, a large capacity storage is required. If a large amount of vital data is to be transmitted to an external device to be accessible from a doctor or a health instructor, a channel established with the external device is heavily loaded and a large amount of power is consumed.

BRIEF DESCRIPTION OF THE DRAWINGS

FIG. 1 is a block diagram illustrating a user terminal according to a first embodiment.

FIG. 2 is a diagram illustrating the appearance of the user terminal in FIG. 1.

FIG. 3 is a diagram illustrating a vital information management system including the user terminal in FIG. 1.

DETAILED DESCRIPTION

Figure 4:
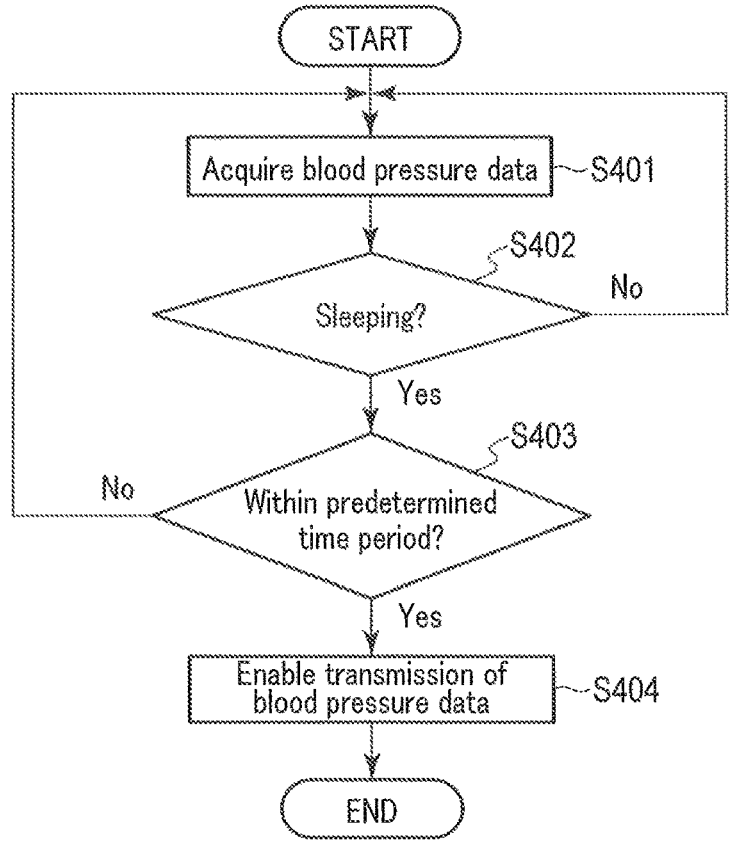
FIG. 4 is a flowchart illustrating operations performed by the user terminal in FIG. 1.

According to an embodiment, a user terminal includes a transmission controller and a communicator. The transmission controller controls whether or not to enable transmission of vital data obtained by measuring vital information about a user, based on whether or not any of one or more transmission conditions is satisfied. The communicator the vital data when the transmission of the vital data was enabled.

According to an embodiment, it is possible to reduce the amount of transmission data from a user terminal to an external device.

Embodiments will be described below with reference to the drawings. In the description below, elements which are the same as or similar to the already described elements are denoted by the same or similar reference numerals, and redundant descriptions will be basically omitted.

First Embodiment

A user terminal according to a first embodiment may be, for example, a watch-type wearable terminal as illustrated in FIG. 2. For example, this user terminal 100 displays information displayed on a general clock such as current date and current time, and further displays vital information about the user such as Systolic Blood Pressure (SYS), Diastolic Blood Pressure (DIA), and pulse rate PULSE. The user terminal 100 can continuously measure the vital information about the user, for example, on a beat-to-beat basis, and display the latest SYS and DIA.

The user terminal 100 may be connected to a smart device (typically, a smartphone or a tablet) 200 as illustrated in FIG. 3. The smart device 200 charts and displays vital data transmitted by the user terminal 100, and transmits the vital data to the server 300 via a network NW. The smart device 200 may have an application installed to manage vital data.

The server 300 accumulates the vital data transmitted from the user terminal 100 or the smart device 200. The server 300 may transmit the vital data of a user to be used for health guidance or diagnosis of the user, in response to access from a Personal Computer (PC) or the like installed in a medical institution, for example. In addition, transmission conditions to be described later may be set in the user terminal 100 from a PC installed in a medical institution via the network NW (and the smart device 200).

As illustrated in FIG. 1, the user terminal 100 according to the first embodiment includes a vital sensor 110, an accelerometer 121, an environment sensor 130, a microphone 122, a clock 123, a user input 124, a sleep determiner 140, a transmission controller 150, a transmission condition storage 160, a communicator 170, and a display 180.

The vital sensor 110 obtains vital data by measuring (for example, continuously measuring) vital information about the user, and transmits the vital data to the communicator 170 and the display 180. The vital sensor 110 includes at least a blood pressure sensor 111 that obtains blood pressure data by measuring (continuously measuring, for example) the user's blood pressure. Thus, the vital data at least includes blood pressure data. The blood pressure data may include, for example, but not limited to, systolic blood pressure and diastolic blood pressure values per beat. The vital data can further include electrocardiogram data, heart rate data, pulse wave data, pulse data, body temperature data, and the like. Each vital data can be associated with measurement time set based on time information received from the clock 123.

The blood pressure sensor 111 can include a blood pressure sensor (hereinafter, referred to as a continuous blood pressure sensor) capable of continuously measuring the blood pressure of the user on a beat-to-beat basis. The continuous blood pressure sensor may continuously measure the blood pressure of the user based on Pulse Transit Time (PTT), or may employ tonometry or other techniques to implement the continuous measurement.

The blood pressure sensor 111 can include, in addition to the continuous blood pressure sensor, a blood pressure sensor (hereinafter, referred to as a non-continuous blood pressure sensor) incapable of implementing the continuous measurement. The non-continuous blood pressure sensor measures the user's blood pressure using, for example, a cuff as a pressure sensor (oscillometry).

Non-continuous blood pressure sensors (oscillometric blood pressure sensors in particular) tend to have higher measurement accuracy than continuous blood pressure sensors. In view of this, the blood pressure sensor 111 may measure the blood pressure data with higher accuracy in the following manner, for example. Specifically, the non-continuous blood pressure sensor may be activated to operate instead of the continuous blood pressure sensor, with the activation triggered by satisfaction of a predetermined condition (for example, a condition satisfied when the user's blood pressure data measured by the continuous blood pressure sensor indicates a predetermined high risk state).

The accelerometer 121 detects acceleration received by the accelerometer 121 to obtain three-axis acceleration data. This acceleration data can be used to estimate the activity state (posture and/or action) of the user wearing the user terminal 100. The accelerometer 121 transmits the acceleration data to the sleep determiner 140. The acceleration data may be associated with the measurement time set based on the time information received from the clock 123.

The user terminal 100 may include a gyro sensor instead of or in addition to the accelerometer 121. The gyro sensor detects rotation and obtains angular velocity data. This angular velocity data can be used to estimate the activity state of the user wearing the user terminal 100. The gyro sensor transmits the angular velocity data to the sleep determiner 140. The angular velocity data may be associated with the measurement time set based on the time information received from the clock 123.

The environment sensor 130 obtains environmental data by measuring environmental information around the user terminal 100, and sends the environmental data to the transmission controller 150 and the display 180. The environment sensor 130 includes at least a temperature sensor 131 that obtains temperature data by measuring the temperature around the user terminal 100. Thus, the environmental data at least includes the temperature data. The environmental data may further include humidity data, barometric pressure data, illuminance data, and the like. Each environmental data may be associated with the measurement time set based on the time information received from the clock 123.

The microphone 122 captures sound around the user terminal 100, converts the sound into an electrical signal (hereinafter referred to as a sound signal), and transmits the sound signal to the sleep determiner 140. The microphone 122 may capture the user's voice, non-verbal sounds (such as snoring or bruxism, for example) generated from the user, environmental sounds, and the like. The sound signal based on these sounds can be used to estimate the user's activity state. The sound signal may be associated with the acquisition time set based on the time information received from the clock 123.

The clock 123 generates time information indicating the current time at a predetermined interval, and transmits the time information to the vital sensor 110, the accelerometer 121 (and/or the gyro sensor), the environment sensor 130, the microphone 122, the transmission controller 150, and the display 180. The time information can be used as the measurement time of vital data obtained by the vital sensor 110, the measurement time of acceleration data obtained by the accelerometer 121 (and/or angular velocity data by a gyro sensor), the measurement time of environmental data obtained by the environment sensor 130, the generation time of the sound signal obtained by the microphone 122, and the like.

The clock 123 may have a calendar function. Thus, the clock 123 may generate date information representing today's date, for example, and transmit it to the transmission controller 150 and the display 180. For example, the date information is useful for the analysis of vital information, because blood pressure may fluctuate differently among days of the week and seasons in addition to the regular daily fluctuation.

The user input 124 is a button, a dial, a crown, or the like for receiving user input. Alternatively, a combination of the user input 124 and the display 180 described later may be implemented using, for example, a touch screen. The user input may include an operation of switching the display screen of the display 180 and an operation of setting a transmission condition described later. The operation of setting a transmission condition may be, for example, an operation of registering a new transmission condition in the transmission condition storage 160, or an operation of changing or deleting the transmission condition registered in the transmission condition storage 160.

For example, the user may perform an operation of setting his or her habitual sleeping time (bedtime) on the user input 124. The bedtime depends on the user's lifestyle and thus may be set for each day of the week, or may be uniformly settable (for example, from 23 o'clock to 7 o'clock) regardless of the day of the week.

The sleep determiner 140 determines whether the user is in a sleep state using a known technique. The sleep determiner 140 notifies the transmission controller 150 of the determination result.

For example, the sleep determiner 140 may determine whether the user is in the sleep state based on the acceleration data detected by the accelerometer 121 (and/or the angular velocity data detected by the gyro sensor). For example, the sleep determiner 140 estimates the posture of the user based on the acceleration data (and/or angular velocity data). The sleep determiner 140 may determine that the user is in the sleep state if the estimated posture of the user corresponds to a lying state such as lying on his or her back or on his or her stomach.

Furthermore, the sleep determiner 140 may determine whether the user is in the sleep state based on the heart rate data or the pulse data detected by the vital sensor 110. For example, the sleep determiner 140 may determine that the user is in the sleep state when the heart rate or the pulse rate of the user is equal to or less than the threshold. This threshold may be set based on, for example, statistics on the user's heart rate or pulse rate. In general, during sleep, the heart rate and pulse rate of the user tend to be low because the parasympathetic nerve is dominant.

Furthermore, the sleep determiner 140 may determine whether the user is in the sleep state based on the sound data (or the feature quantity thereof) acquired by the microphone 122. For example, the sleep determiner 140 may determine that the user is in the sleep state when the sound data (or the feature quantity thereof) from the microphone 122 matches reference sound data (or the feature quantity thereof), corresponding to snoring, prepared in advance. This reference sound data can be prepared by pre-recording the snoring of the user or others.

The sleep determiner 140 may use some or all of the acceleration data (and/or angular velocity data), the heart rate data, the pulse data, and the sound data to determine whether the user is in the sleep state. Alternatively, the sleep determiner 140 may determine whether the user is in the sleep state using parameters other than these pieces of data.

The sleep determiner 140 may supplementally use illuminance data detected by the environment sensor 130 to determine whether the user is in the sleep state. For example, the sleep determiner 140 may determine that the user is in the sleep state based on a less-stringent criteria, in a case that the illuminance data is lower than a threshold (dark environment), compared with other cases (bright environment).

The transmission controller 150 reads one or more transmission conditions stored in the transmission condition storage 160, and determines whether at least one of the transmission conditions is satisfied. The transmission conditions can be defined in advance using, for example, some or all of the measurement time of vital data, the user's activity state (including sleep state), the environmental temperature and the like. The transmission conditions may be defined using parameters not exemplified in this document. When at least one of the transmission conditions is satisfied, the transmission controller 150 enables the transmission of the vital data, which was transmitted from the vital sensor 110 to the communicator 170.

The transmission condition may include a first transmission condition that is satisfied when the user is in the sleep state. Upon being notified of a determination result indicating that the user is in the sleep state from the sleep determiner 140, the transmission controller 150 determines that the first transmission condition is satisfied, and enables the transmission of the vital data.

The transmission condition may include a second transmission condition that is satisfied when the user is in the sleep state and the measurement time of the vital data is within a time period defined in advance. Upon being notified of a determination result indicating that the user is in the sleep state from the sleep determiner 140 with the measurement time associated with the vital data included within the time period defined in advance, the transmission controller 150 determines that the second transmission condition is satisfied and enables the transmission of the vital data.

The time period defined in advance may be bedtime. Monitoring of blood pressure during bedtime is useful for determining whether the user has any signs of nocturnal hypertension. The nocturnal hypertension is one type of masked hypertension in which the average systolic blood pressure and diastolic blood pressure at night are 120 mmHg or more and 70 mmHg or more, respectively.

For the second transmission condition, the transmission controller 150 operates, for example, as shown in FIG. 4. The transmission controller 150 acquires vital data (in particular, blood pressure data) as a process target from the vital sensor 110 (step S401).

The transmission controller 150 refers to the determination result notified from the sleep determiner 140, and checks whether the user was in the sleep state at the measurement time of the vital data (step S402). If the user was in the sleep state, the process proceeds to step S403. If not, the transmission controller 150 does not enable the transmission of the vital data as the process target, and the process returns to step S401.

In step S403, the transmission controller 150 checks whether or not the measurement time of the vital data is within a predetermined time period defined in the second transmission condition. If the measurement time is within the predetermined time period, the process proceeds to step S404. Otherwise, the process returns to step S401. In step S404, the transmission controller 150 enables the transmission of vital data as the process target, and the operation in FIG. 4 is terminated.

The transmission conditions may include, for example, a third transmission condition that is satisfied when the fluctuation of the ambient temperature in the most recent unit time exceeds a threshold. Blood pressure is known to rise due to temperature fluctuations (low temperature in particular). For example, what is known as heat shock, which could even be fatal, might occur when a person is exposed to a sudden temperature change in cases such as moving out from (or into) an air-conditioned room or bathing in winter. Therefore, monitoring of blood pressure before and after the sudden temperature fluctuations is useful for recognizing whether the user has any signs of heat shock. The threshold is, for example, 10 degrees, but is not limited to this.

Figure 5:
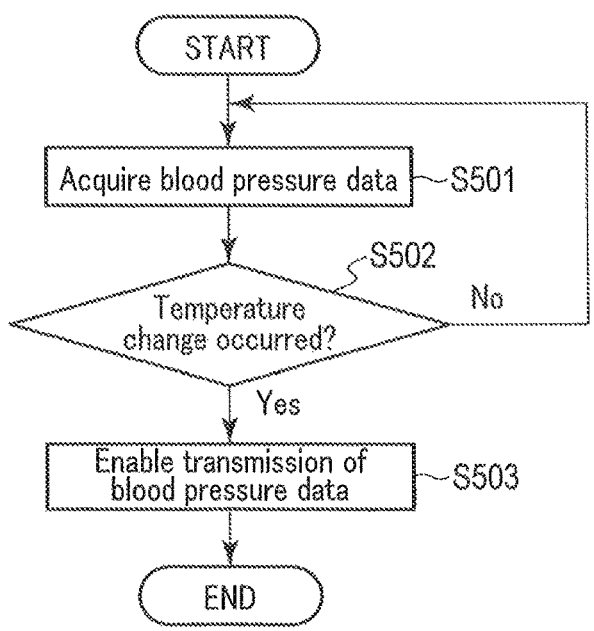
FIG. 5 is a flowchart illustrating operations performed by the user terminal in FIG. 1.

For the third transmission condition, the transmission controller 150 operates, for example, as shown in FIG. 5. The transmission controller 150 acquires vital data (in particular, blood pressure data), as a process target, from the vital sensor 110 (step S501).

The transmission controller 150 refers to the latest temperature data received from the environment sensor 130, and checks whether a temperature change occurred immediately before the measurement time of the vital data (step S502). If the temperature change occurred, the process proceeds to step S503. If not, the transmission controller 150 does not enable the transmission of the vital data as the process target, and the process returns to step S501. In step S503, the transmission controller 150 enables the transmission of the vital data as the process target, and the operation in FIG. 5 is terminated.

The transmission conditions are not limited to the above example. For example, early morning hypertension, which is a type of masked hypertension, includes early morning hypertension (hereinafter referred to as peculiar early morning hypertension) involving peculiarly high early morning blood pressure compared to other time zones. This peculiar early morning hypertension is known to be a risk independent of morning and evening blood pressure average values. The peculiar early morning hypertension may be diagnosed based on a comparison between blood pressure at the time when the user goes to bed and early morning blood pressure. In view of this, the transmission controller 150 may identify blood pressure data at the time when the user goes to bed (for example, immediately before transitioning to the sleep state) based on the sleep state notified from the sleep determiner 140, and enable the transmission of the blood pressure data. Furthermore, the transmission controller 150 may enable the transmission of the blood pressure data when the measurement time associated with the blood pressure data is within an early morning time zone defined in advance. Thus, monitoring of the blood pressure at the time when the user goes to bed and early morning blood pressure is useful for determining whether the user has signs of peculiar early morning hypertension.

For example, sharp blood pressure fluctuation (blood pressure surge) may be triggered by hypoxia during episodes of Sleep Apnea Syndrome (SAS). Thus, monitoring of blood pressure surges is useful for recognizing the severity of the user's SAS symptom. Such specific blood pressure fluctuations may be patterned in advance, and a transmission condition that is satisfied if the fluctuations in blood pressure data match the pattern may be defined.

The transmission condition storage 160 stores the transmission conditions. The transmission conditions may be set at the time of manufacture of the user terminal 100, may be received by the communicator 170 from an external device via a network (for example, the Internet), or may be set based on the user input received by the user input 124. For example, a doctor may operate an external device (a PC installed at a medical institution, for example) to set transmission conditions in order to diagnose whether the user has masked hypertension.

The communicator 170 exchanges data with an external device via a network. The communicator 170 may perform one of wireless communications and wired communications or both. For example, the communicator 170 may perform near field communications using Bluetooth (registered trademark) etc. with the smart device 200, for example.

At least whether or not the transmission of the vital data by the communicator 170 is enabled is under control by the transmission controller 150. When the transmission controller 150 enables the transmission of the vital data, the communicator 170 transmits the vital data to the external device.

The display 180 is, for example, a liquid crystal display, an organic electroluminescence (EL) display, or the like. The display 180 can notify the user of various pieces of information by displaying screen data. Specifically, the display 180 may display vital information (such as blood pressure, electrocardiogram, heart rate, pulse wave, pulse rate, and body temperature, for example), acceleration data, angular velocity data, activity amount information (such number of steps and calorie consumption calculated based on acceleration data (and/or angular velocity), for example), sleep information (such as sleep time, for example), environmental information (such as temperature, humidity, and atmospheric pressure, for example), current time, calendar, and the like.

As described above, the user terminal according to the first embodiment transmits the vital data obtained by measuring (for example, continuously measuring) vital information about the user to an external device such as a smart device or a server only when the transmission condition is satisfied, instead of constantly transmitting the vital data. Specifically, the user terminal transmits, to an external device, vital data that is likely to be significant, such as (night) sleep blood pressure, blood pressure at the time when the user goes to bed, early morning blood pressure, and blood pressure before and after the occurrence of sharp temperature fluctuation, for example, and omits the transmission of other vital data. Thus, this user terminal can achieve a smaller power consumption and a load on a channel, involved in the vital data transmission, compared with a case where the vital data is entirely transmitted. Furthermore, reduction of the capacity of the storage for accumulating the vital data can also be achieved, if only the vital data that is likely to be significant is stored.

The embodiments described above are merely illustrative examples to assist in understanding the inventive concept, and are not intended to limit the scope of the present invention. Various components can be added to, deleted from, or converted in the embodiments without departing from the gist of the present invention.

The various functional units described in the above embodiments may be implemented with a circuit. The circuit may be a dedicated circuit that implements a specific function, or may be a general-purpose circuit such as a processor that is connected to a memory and executes a predetermined program stored in the memory.

At least a part of the processing in each of the above-described embodiments can also be implemented with a general-purpose computer serving as basic hardware. The program for realizing the above process may be stored in a computer readable recording medium to be provided. The program is stored in the recording medium as a file in an installable format or as a file in an executable format. The recording medium includes a magnetic disk, an optical disk (such as CD-ROM, CD-R, or DVD), a magneto-optical disk (such as MO), a semiconductor memory, and the like. The recording medium may be any medium that can store the program to be readable by a computer. Furthermore, a program for implementing the processing described above may be stored on a computer (server) connected to a network such as the Internet, and may be downloaded to a computer (client) via the network.

The invention claimed is:

1. A user terminal comprising:
   a memory;
   a processor connected to the memory;
   a blood pressure sensor configured to measure blood pressure of a user to obtain blood pressure data; and
   a temperature sensor configured to measure temperature to obtain temperature data, the temperature representing ambient temperature, wherein
   the processor is configured to:
      control whether or not to enable transmission of the blood pressure data based on whether or not any of one or more transmission conditions is satisfied; and
      transmit the blood pressure data when the transmission of the blood pressure data was enabled, and
   the one or more transmission conditions include at least a transmission condition satisfied when a fluctuation of the temperature in a latest unit time of measurement time of the blood pressure data exceeds a threshold, the temperature being indicated by the temperature data.

2. The user terminal according to claim 1, wherein the one or more transmission conditions further include a transmission condition defined in advance using at least one of measurement time of the blood pressure data and an activity state of the user.

3. The user terminal according to claim 1, wherein the processor is further configured to determine whether or not the user is in a sleep state, and
   the one or more transmission conditions further include a first transmission condition satisfied when the user is in the sleep state.

4. The user terminal according to claim 1, wherein the processor is further configured to determine whether or not the user is in a sleep state, and
   the one or more transmission conditions include a second transmission condition satisfied when the user is in the sleep state and measurement time of the blood pressure data is within a time period defined in advance.

\* \* \* \* \*